United States Patent [19]

Harrison

[11] Patent Number: 5,219,525

[45] Date of Patent: Jun. 15, 1993

[54] APPARTUS AND METHOD FOR DETERMINING IMPURITIES IN LIQUIDS

[76] Inventor: Phillip D. Harrison, 24205 Mt. Olive, Flat Rock, Mich. 48134

[21] Appl. No.: 580,828

[22] Filed: Sep. 11, 1990

[51] Int. Cl.⁵ .................. G01N 21/00; B01L 11/00
[52] U.S. Cl. .................................. 422/58; 422/68.1;
422/101; 210/238; 210/464; 210/477;
210/DIG. 17
[58] Field of Search ............... 422/58, 101, 68.1;
435/299, 311; 210/232, 238, 464, 473, 474, 477,
497.3, DIG. 17

[56] References Cited

U.S. PATENT DOCUMENTS

| | | |
|---|---|---|
| 1,489,039 | 4/1924 | Mack . |
| 2,197,909 | 4/1940 | Wendler ................................ 73/51 |
| 2,307,318 | 1/1943 | Kinney ................................ 73/51 |
| 2,672,431 | 3/1954 | Goetz ................................ 195/139 |
| 2,935,384 | 5/1960 | Schalm et al. ........................ 23/258 |
| 3,160,000 | 12/1964 | Mosher ................................ 73/61 |
| 4,675,110 | 6/1987 | Fay ................................ 210/474 |
| 4,689,147 | 8/1987 | Leoncavallo et al. ............... 210/232 |
| 4,698,210 | 10/1987 | Solazzi ................................ 422/102 |
| 4,797,260 | 1/1989 | Parker ................................ 422/101 |
| 4,912,034 | 3/1990 | Kalra et al. ........................ 422/101 |
| 5,008,080 | 2/1990 | Brown, III et al. ................ 422/101 |
| 5,047,215 | 9/1991 | Manns ................................ 435/311 |
| 5,073,340 | 12/1991 | Covington ............................ 422/58 |

*Primary Examiner*—James C. Housel
*Assistant Examiner*—Jan M. Ludlow
*Attorney, Agent, or Firm*—Basile and Hanlon

[57] ABSTRACT

An apparatus for determining impurities in liquids has a funnel having a first end and a smaller diameter outlet having an outer periphery. A funnel holder releasably holds the funnel. A portable test film carrier, removably engageable with the funnel holder, holds the test film. The test film carrier includes a mechanism for removably securing and releasably tensioning the test film within the test film carrier. A uniform test area is provided on the test film. The apparatus provides a high degree of test result reproducibility.

14 Claims, 3 Drawing Sheets

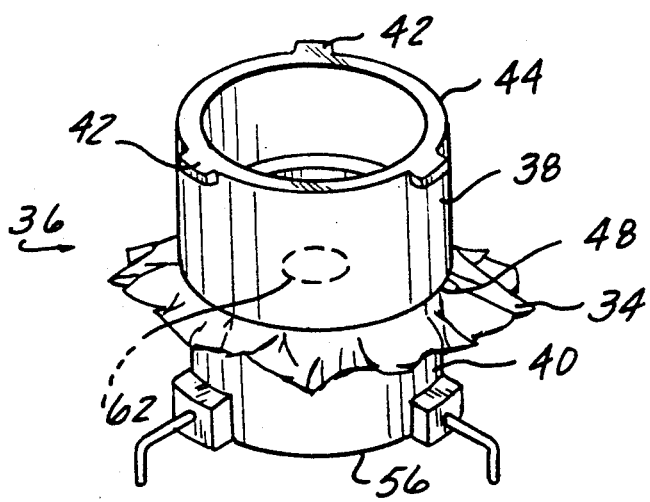
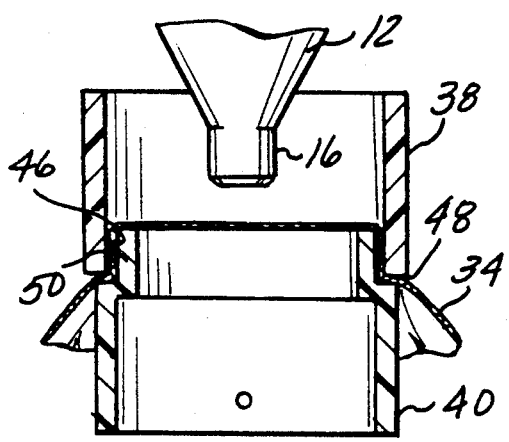
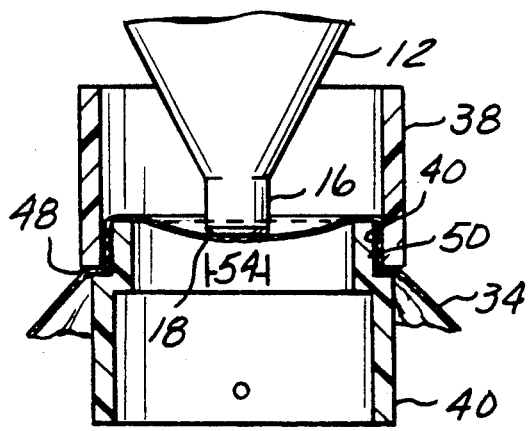
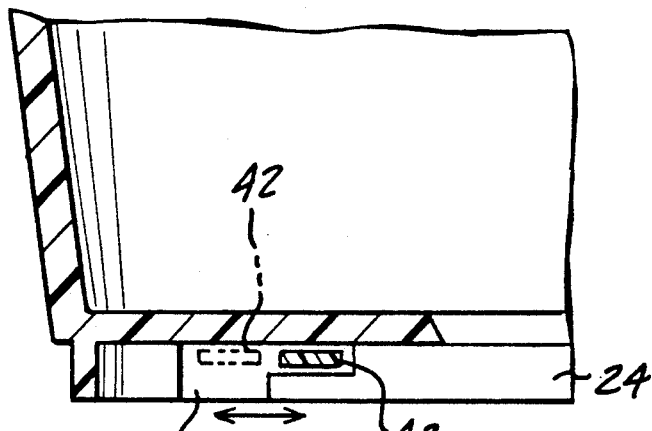
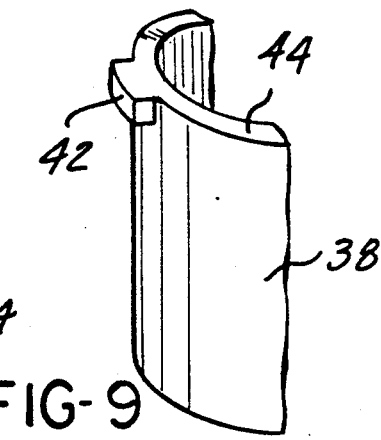

APPARATUS AND METHOD FOR DETERMINING IMPURITIES IN LIQUIDS

BACKGROUND OF THE INVENTION

1. Field of the Invention

The present invention relates generally to an apparatus and method for determining impurities in liquids, and more specifically, to such an apparatus which can give a reproducible impurity particle count per test area.

2. Description of the Relevant Art

In recent years, testing of consumer products, both wholesale and retail, has become extremely important. Consumers need to know as nearly as possible the exact components of a particular consumer good and relative percentages of each component. In the food area, this has become increasingly important as more and more people become health conscious—they want to know exactly what is in each food product and the purity levels of that food product before they will make the purchase.

In other industries, suppliers must also determine exact contents and purity levels of products in order to inform manufacturers before purchasing. In this way, manufacturers can determine ahead of time which suppliers' material will work best for a particular manufacturer's end product. This decision is made by determining what substances must be in the material and what purity level is required for maximum performance at least cost in the end product.

Thus, it would be desirable to obtain a testing apparatus which would meet the need for testing materials such as liquids in so many facets of industry. Such an apparatus should be lightweight, simple to use and easily carried from lab bench to microscope. Such an apparatus would also be equally useful in the field as well as in the laboratory, and at the same time provide reproducible test results. It would further be desirable to provide such an apparatus which is highly resistant to breakage, and has low cost, easily replaceable components.

SUMMARY OF THE INVENTION

The present invention meets all the needs enumerated above by providing an apparatus for determining impurities in liquids which comprises a funnel having a first end and a smaller diameter outlet having an outer periphery. Means are provided for holding the funnel. The apparatus further comprises means, removably engageable with the funnel holding means, for portably carrying test film. Means are provided for removably securing and releasably tensioning the test film within the test film carrying means. Also, means are provided for defining a uniform test area on the test film.

BRIEF DESCRIPTION OF THE DRAWINGS

Other objects and features of the invention will become apparent by reference to the following specification and drawings, in which:

FIG. 5 is a perspective view of the portable test film carrier assembly ready to be moved to a microscope, with the test liquid sample shown in hidden line;

FIG. 6 is a cross sectional view of the test film carrier before the funnel is in the fully assembled position;

FIG. 7 is the view of FIG. 6 showing the funnel in the fully assembled position, directly contacting and applying a constant pressure to the test film;

FIG. 8 is an exploded cut-away cross sectional view of the lower portion of the funnel holder showing a funnel holder slot and the test carrier projection in both the locked and unlocked positions; and FIG. 9 is an exploded cut-away perspective view of the test carrier first portion showing a projection.

DETAILED DESCRIPTION OF THE PREFERRED EMBODIMENT

Figure 1:
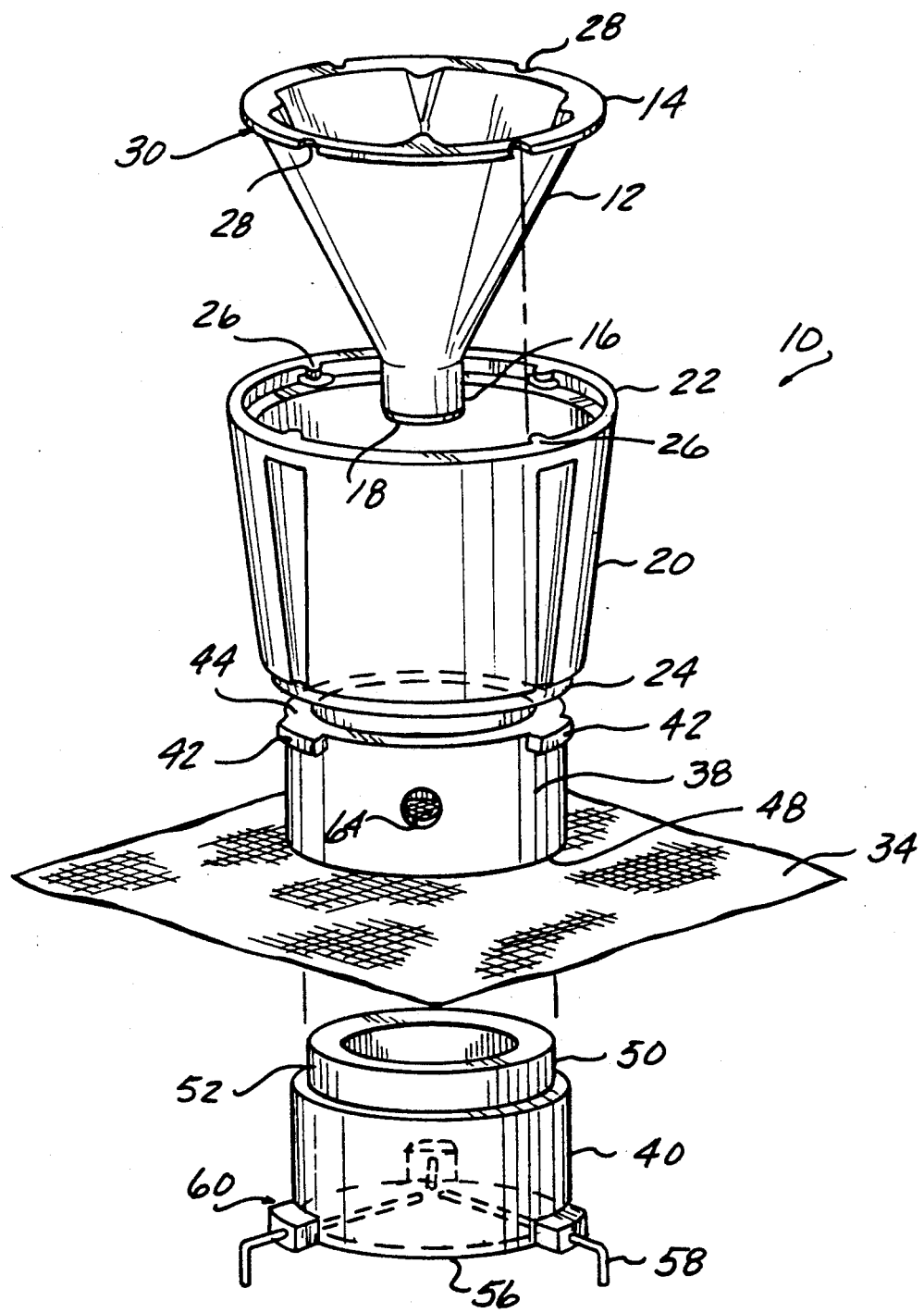
FIG. 1 is an exploded perspective view of the testing apparatus of the present invention.

Referring now to FIG. 1, an apparatus for determining impurities in liquids is designated generally as 10. The apparatus comprises a funnel 12 having a first end 14 and a smaller diameter outlet 16 having an outer periphery 18.

Figure 3:
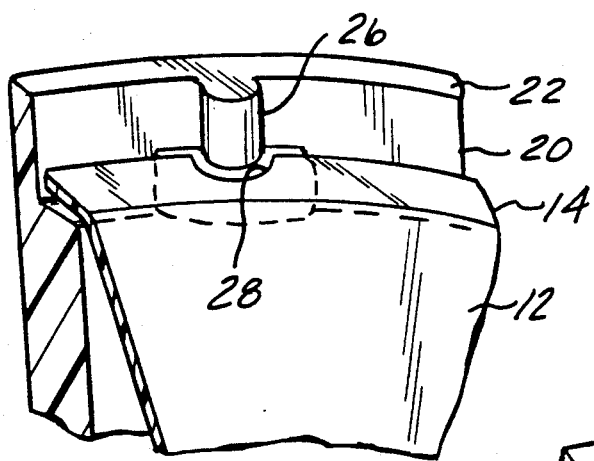
FIG. 3 is an enlarged detail cross sectional perspective view showing the funnel slot and funnel holder projection in the unlocked position.
Figure 4:
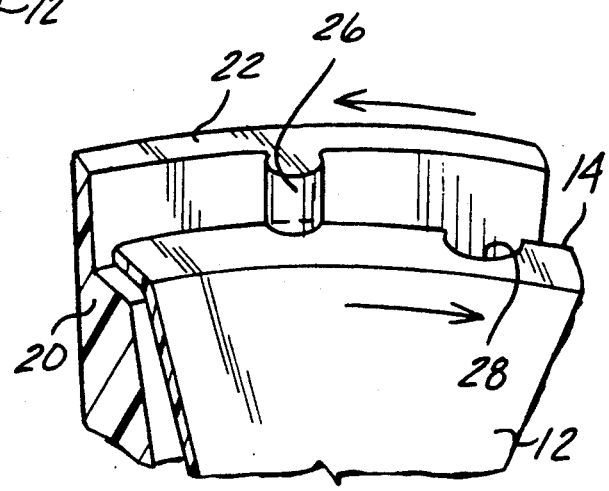
FIG. 4 shows the view of FIG. 3 in the locked position.

Means are provided for holding funnel 12. This means may be any conventionally suitable holding means which is adapted to hold the particular funnel 12 chosen. In the preferred embodiment, this funnel holding means comprises a funnel holder 20 having a first end 22 and a second end 24. Funnel holder first end 22 has projections 26 for interlocking engagement with funnel slots 28 formed in the outer periphery 30 of funnel first end 14. FIGS. 3 and 4 show the interlocking arrangement of funnel slots 28 with funnel holder projections 26. A funnel holder second end 24 has slots 32 formed therein, as best seen in FIG. 8.

The apparatus 10 further comprises test film 34 having a predetermined mesh size. Means, removably engageable with the funnel holding means, portably carries test film 34. This portable carrying means may comprise any suitable carrying means which will carry the test film 34 away from funnel holder 20 and to an optical instrument such as a microscope (not shown). In the preferred embodiment, this portable carrying means comprises a test film carrier 36 as best seen in FIG. 5. Test film carrier 36 has a first portion 38 and a second portion 40. First portion 38 has projections 42 at a first end 44 thereof. Projections 42 are interlockingly engageable with slots 32 in the funnel holder second end 24.

Means are provided for removably securing and releasably tensioning test film 34 within the test film carrying means. This securing and tensioning means may comprise any suitable means which would render test film 34 taut and immovable while in a suitable test film carrier. In the preferred embodiment, this means comprises a receiving portion 46 formed in the carrier first portion 38 at a second end 48 thereof. A recessed portion 50 is adapted to closely fit within receiving portion 46. Recessed portion 50 is formed on the carrier second portion 40 at a first end 52 thereof, wherein test film 34 is kept taut when secured between recessed portion 50 and receiving portion 46.

Figure 2:
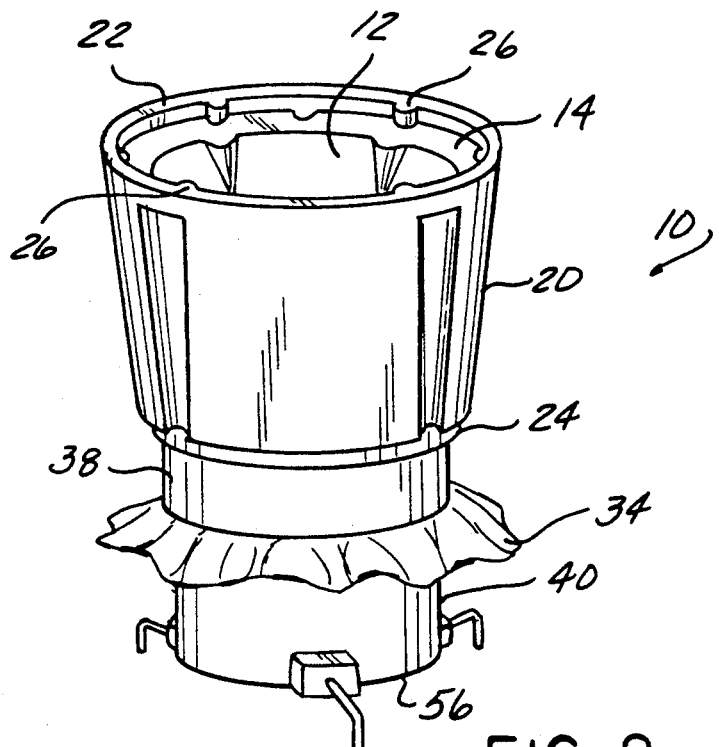
FIG. 2 is a perspective view of the present invention in the assembled position.

Test apparatus 10 further comprises means for defining a uniform test area 54 as shown in FIG. 7. This means may also comprise any suitable means which would achieve reproducible test results in the apparatus 10. In the preferred embodiment, this defining means is accomplished by the funnel outlet 16, in the assembled position as shown in FIGS. 2 and 7, directly contacting, and applying a constant pressure to test film 34 such that uniform test area 54 is defined by the outlet outer periphery 18 contacting test film 34. This is accomplished in the preferred embodiment by selecting a funnel 12 of a shape and size such that the funnel outlet 16 will contact test film 34 as described above. In the preferred embodiment, the pressure applied by the funnel outlet 16 is less than or equal to a pressure which would enlarge the predetermined mesh size of test film 34. This is in order to prevent impurities from falling through test film 34. However, if this is not a consideration for a particular user, greater pressure such that the mesh size will expand, could be used.

Test apparatus 10 may further comprise means, formed on the carrier second portion 40 at a second end 56 thereof, for mounting apparatus 10 to a waste collection container (not shown). This optional mounting means may comprise any suitable conventionally known mounting means, but in the preferred embodiment, this means comprises legs 58 attached by a suitable means 60 to the second end 56 of carrier second portion 40.

The various components of testing apparatus 10 may be formed of any suitably rigid material, such as a molded polymeric material. In the preferred embodiment, the funnel is formed of high density polyethylene while the funnel holder and test film carrier are formed by injection molding a 30% glass reinforced polyester alloy such as the material commercially available from General Electric, Inc. under the tradename VALOX No. 508.

A method for determining impurities in a liquid comprises the following steps. The technician selects a test film 34 having a mesh size sufficient to allow the liquid to be tested to flow through while retaining any impurities 62 found in the liquid. The test film 34 is next tautly secured in the test film carrier 36. A funnel 12 having an outlet 16 with an outer periphery 18 is placed into the funnel holder 20. The funnel holder 20 is attached to the test film carrier 36 in a manner such that the funnel outlet 16 directly contacts, and applies a constant pressure to test film 34 such that a uniform test area 54 is defined by the outlet outer periphery 18 contacting test film 34. The liquid is poured into funnel 12 in a manner such that the liquid contacts and flows through the test film test area 54, with the impurities 62 being trapped by the test film within test are 54. The test film carrier 36 is removed from funnel holder 20, and is placed in an optical instrument, such as a microscope (not shown) which will sufficiently magnify test area 54 such that the number of impurity particles 62 per test area may be determined. The test film carrier 36 is then removed from the optical instrument, and test film 34 is removed from test film carrier 36. Test film 34 may then be discarded.

If any non-impurity component of the liquid remains on the test film test area 54 such that it would interfere with the determination of the impurity particle count, then the technician must use a solvent to flush away these non-impurity components before taking test film carrier 36 to the microscope. The solvent used would be any suitable solvent of a type, and in an amount sufficient to rinse away any non-impurity components. In addition, if thick paints or other materials having colored components are tested, these materials may bleed beyond the test area 54. In such cases, it is preferred that test film carrier first portion 38 have a through bore 64 as shown in FIG. 1. In this manner, after the material to be tested has gone through the funnel and hit test area 54, the technician may flush solvent through the bore 64. The solvent will hit the outside of funnel 12, drop down on test film 34 and wash away any test material which has bled outside the test area 54.

The test apparatus 10 can be used to test any or all liquids. Depending on the density of the liquid, the test film mesh size selected will vary. The thicker the liquid, the coarser mesh size needed. Or, the technician could use a finer mesh size and dilute the liquid to be tested. Examples of liquids to be tested are oils, solvents, gasoline, paints, water, etc. The impurities that one would test for could include any and all generally known impurities, including metals, fibers, rock, dirt, etc.

Apparatus 10 may also be used without funnel 12 if the liquid is such that it would not readily flow through funnel 12. The mesh size for the test film 34 would therefore have to be very coarse.

The present invention, due to the uniform test area 54, gives a high degree of reproducibility. Since the normal measure of impurity is number of impurity particles per set area, it is important to have a known test area. Every time the present test apparatus is used, the liquid to be tested is essentially concentrated in the uniform test area 54, which same area is inspected under the microscope. In this manner, since the test area stays essentially uniform, there is a higher degree of reproducibility and less chance of error between multiple tests on the same liquid.

In addition, since the apparatus 10 is very sturdy, there is a lesser chance of breakage, unlike with sensitive, expensive analyzing equipment. Also, if a certain liquid soils the funnel such that it cannot be reused, the funnel may be replaced at a relatively low cost.

While certain embodiments of the invention have been described in detail above, it is to be understood that the foregoing description is merely exemplary and not limitative and the true scope of the invention is that defined in the following claims.

What is claimed is:

1. An apparatus for determining impurities in liquids, comprising:
   a funnel having a first end and a smaller diameter outlet having an outer periphery;
   funnel holding means, interlockingly, removably engaged with the funnel, for holding the funnel;
   test film carrying means, removably engaged with the funnel holding means, portably carrying a test film;
   securing and tensioning means, disposed within the test film carrying means, for removably securing and releasably tensioning the test film;
   defining means for defining a uniform test area on the test film such that the defining means separates the test film into first and second distinct areas, the first area being the uniform test area and the second area being outside the uniform test area, the uniform test area trapping the impurities to be determined; and
   introducing means, located on the test film carrying means and above the test film, for introducing a flushing liquid to the second test film area outside the uniform test area such that the trapped impurities within the first uniform test area remain substantially untouched by the flushing liquid.

2. The apparatus as defined in claim 1 wherein the funnel first end has an outer periphery with slots formed therein and the funnel holding means comprises a funnel holder having a first end and a second end, the funnel holder first end having projections for interlocking engagement with the funnel slots.

3. The apparatus as defined in claim 1 wherein the test film has a predetermined mesh size.

4. The apparatus as defined in claim 1 wherein the introducing means comprises a through bore.

5. The apparatus as defined in claim 1 wherein the funnel is formed of high density polyethylene.

6. The apparatus as defined in claim 1 wherein the funnel outlet directly contacts and applies a constant pressure to the test film such that the first uniform test area is defined by the outlet outer periphery contacting the test film.

7. The apparatus as defined in claim 6 wherein the pressure is less than or equal to a pressure which would enlarge a predetermined mesh size of the test film.

8. The apparatus as defined in claim 1 wherein the test film carrying means comprises a test film carrier having a first and second portion, and the funnel holding means comprises a funnel holder having a first end and a second end, the funnel holder second end having slots, 9. The apparatus as defined in claim 8 wherein the securing and tensioning means comprises:
 a receiving portion formed in the film carrier first portion at a second end thereof; and
 a recessed portion adapted to closely fit within the receiving portion, the recessed portion being formed on the carrier second portion at a first end thereof;
wherein the test film is kept taut when secured between the recessed portion and the receiving portion.

10. The apparatus as defined in claim 8 further comprising mounting means, formed on the film carrier second portion at one end thereof, for mounting the apparatus to a waste collection container.

11. An apparatus for determining impurities in liquids, comprising:
 a funnel having a first end having an outer periphery with slots formed therein, the funnel further having a smaller diameter outlet having an outer periphery;
 a funnel holder having a first end and a second end, the funnel holder first end having projections for releasable interlocking engagement with the funnel slots, the funnel movable between a first funnel position wherein it is securely received within the funnel holder, the funnel holder first end projections being interlockingly engaged with the funnel slots, the funnel holder second end having slots formed therein, and a second funnel position wherein the funnel is removed from the funnel holder;
 a portable test film carrier, releasably holding a test film having a predetermined mesh size, the test film carrier having a first and second portion, the first portion having projections at a first end thereof for releasable interlocking engagement with the funnel holder slots, the test film carrier movable between a first carrier position wherein it is securely attached to the funnel holder, the first portion first end projections being interlockingly engaged with the funnel holder slots, and a second carrier position wherein the test film carrier is removed from the funnel holder;
 a receiving portion formed in the carrier first portion at a second end thereof;
 a recessed portion adapted to closely fit within the receiving portion, the recessed portion being formed on the carrier second portion at a first end thereof, the test film movable between a first test film position wherein it is kept taut, secured between the recessed portion and the receiving portion, and a second test film position wherein the test film is removed from the test film carrier;
 a uniform test area on the test film, the funnel being of a shape and size such that, in the first funnel position, the funnel outlet directly contacts, and applies a constant pressure to the test film such that the uniform test area is defined by the outlet outer periphery contacting the test film and the outlet outer periphery thereby separates the test film into first and second distinct areas, the first area being the uniform test area and the second area being outside the uniform test area, the uniform test area trapping the impurities to be determined; and
 introducing means, located on the test film carrier and above the test film, for introducing a flushing liquid to the second test film area outside the uniform test area such that the trapped impurities within the first uniform test area remain substantially untouched by the flushing liquid.

12. The apparatus as defined in claim 11 wherein the pressure is less than or equal to a pressure which would enlarge the predetermined mesh size of the test film.

13. The apparatus as defined in claim 11 further comprising mounting means, formed on the film carrier second portion at a second end thereof, for mounting the apparatus to a waste collection container.

14. The apparatus as defined in claim 11 wherein the funnel is formed of high density polyethylene, and the funnel holder and test film carrier are formed from an injection molded 30% glass reinforced polyester alloy.

* * * * *